United States Patent [19]
Maas, III

[11] Patent Number: 5,682,708
[45] Date of Patent: Nov. 4, 1997

[54] RAPID GENERATION ADVANCEMENT IN WINTER WHEAT

[75] Inventor: Frederick B. Maas, III, W. Lafayette, Ind.

[73] Assignee: Purdue Research Foundation, West Lafayette, Ind.

[21] Appl. No.: 222,821

[22] Filed: Apr. 5, 1994

[51] Int. Cl.$^6$ ............................. A01H 1/04; A01H 5/00
[52] U.S. Cl. ..................... 47/58; 47/DIG. 1; 800/200; 800/250; 800/DIG. 58
[58] Field of Search ........................... 800/200, 250, 800/DIG. 58; 47/58.01, 58.03, 58.07, DIG. 1

[56] References Cited

PUBLICATIONS

Briggle and Curtis (1987) Wheat and Wheat Improvement:1.
Cartwright and Jones (1953) USDA Farmer's Bull., U.S. Govt. Printing Office, D.C.:1627.
Hudson et al., (1991) Georgia Agric. Exp. Stn. Spec. Publ. No. 70:29.
Hatchett and Gallum, (1970), Ann. Entomol. Soc. Amer. 63:1400.
Patterson et al., (1992) J. Econ. Entomol. 85:307.
Morrison, (1960) Z. VererbLehre 91:141.
McIntosh and Cusick (1987) Wheat and Wheat Improvement:289.
McIntosh and Cusick, 1987.
Allan. 1986. Crop Science. 26: 707–710.
Brule–Babel et al. 1988. Crop Science. 28:879–884.
Sears et al. 1992. Crop Science. 32:506.
Chen et al. 1992. Crop Science. 32:692–696.
Knott, 1987. In Wheat and Wheat Improvement, Heyne, ed. Aronomy Monograph No. 13 (2nd Ed.). Ch. 7A:418–427.
Roberts, Apr. 1990, Genome. 33(2):247–259.

*Primary Examiner*—Douglas W. Robinson
*Assistant Examiner*—Melissa L. Kimball
*Attorney, Agent, or Firm*—Woodard, Emhardt, Naughton, Moriarty & McNett

[57] ABSTRACT

Methods for rapidly advancing wheat generations towards a winter wheat objective, including crossing a winter wheat line with a donor line having a dominant minimal vernalization gene, breeding the offspring from that cross, and selecting to recover wheat plants having the winter growth habit. The breeding process may include selection for the minimal vernalization trait. The offspring resulting from the breeding process may also be crossed with a winter wheat before selection for the winter growth habit. The donor line includes a dominant vernalization gene and also in some cases a gene or genes for a desired trait.

24 Claims, No Drawings

RAPID GENERATION ADVANCEMENT IN WINTER WHEAT

This invention was made with Government support under Grant No. 58-3602-2-202 awarded by the United States Department of Agriculture. The government has certain rights in the invention.

FIELD OF THE INVENTION

This invention relates to breeding of wheat plants. In particular, it relates to methods for rapidly advancing wheat inbreeding generations to enhance breeding programs.

BACKGROUND OF THE INVENTION

Wheat (*Triticum aestivum* L.) is the most important human food crop in the world. Winter wheat is grown worldwide and accounts for more than 60% of U.S. wheat production (Briggle and Curtis (1987) *Wheat and Wheat Improvement*:1). Various cultivars have been developed to accommodate different growing conditions, wheat usages and resistance to disease and insects. Such improved cultivars have been a significant factor in increasing wheat yields and quality as well as stabilizing global wheat production.

Breeding objectives involve creating new genotypes improved in one or more important features. These objectives vary widely because the environmental conditions that affect wheat production and adversities that limit wheat yields differ from one production area to another. The principal categories of improvement objectives include yield potential, yield stability and grain quality as is generally discussed in Poehlman, (1987) *Breeding Field Crops*, Connecticut: A.V.I. Pub. Co. Inc.).

One of the most important breeding objectives in wheat breeding is yield because it affects the economic return to the farmer. Wheat genotypes differ in their inherent yield potential. Several plant characteristics have been associated with higher yield potential. The most important have been greater spike productivity, kernel weight, spike size, and shorter straw. Shorter straw cultivars have been obtained by incorporation of dwarfing genes, such as $Rht_1$ and $Rht_2$. When only one such gene is incorporated, the new wheat cultivar is called a semi-dwarf.

Another important breeding objective, yield stability, is accomplished by breeding for early maturity, lodging and shatter resistance, tolerance to drought and soil stress, and resistance to disease and insect pests. Early wheat is advantaged because it may escape damage from heat, drought, insects, or disease. Early harvest also permits early removal of wheat crop in areas where multiple cropping is practiced. The inheritance of earliness has been reported as being dominant or partially dominant to late maturity and appears to be controlled by a few major genes.

Resistance to lodging, a bending or breaking of the wheat culm, also contributes to a yield stability objective. The development of varieties with short, stout stems has increased the length of time that wheat will stand without breaking. Short stature may be obtained by 1) selecting for quantitative genes that reduce stem length in conventional varieties, 2) the use of dwarfing genes, or 3) combinations of the two groups of genes.

Another element of yield stability is resistance to diseases, such as rust diseases, the smuts, foliage diseases, root rot diseases, and viral diseases. The rust diseases are among the most destructive plant diseases and exist in a gene-for-gene relationship. Resistance to rust disease is dominant over susceptibility.

Several insects are problematic in wheat breeding. The major insect problems include wheat stem sawfly, cereal leaf beetle, green bug, and Hessian fly. Green bug resistance is conferred by a single dominant, biotype-specific gene. The Hessian fly is the most destructive wheat insect pest in the USA. In 1915, before the introduction of resistant cultivars, an outbreak of the Hessian fly caused an estimated $100 million in cross loss (Cartwright and Jones (1953) USDA Farmer's Bull., U.S. Govt. Printing Office, Washington, D.C.:1627). More recently, an estimated loss of $28 million was reported in the State of Georgia (Hudson et al., (1991) Georgia Agric. Exp. Stn. Spec. Publ. No. 70:29.). Virulence in the Hessian fly and antibiosis in the wheat host exist in gene-for-gene relationships (Hatcherr and Gallum, (1970), *Ann. Entomol. Soc. Amer.* 63:1400.). Resistance in the host is usually dominant and virulence in the insect is recessive. Several Hessian fly biotypes have been described that differ in their ability to infest wheats with specific genes for resistance. Genes for resistance and Hessian fly biotypes have been reviewed recently (Patterson et al., (1992) *J. Econ. Entomol.* 85:307.)

Various breeding methods have been used extensively to add specific disease resistance genes to otherwise susceptible cultivars. Unfortunately, new biological forms of the disease pathogen soon arise to which the gene transferred does not confer resistance. This is particularly so when there is a gene-for-gene relationship between the wheat cultivar and the pathogen or pest. The term gene-for-gene relationship refers to an interaction between wheat genotypes which control reaction to the pathogen and the genotypes for pathogenicity in the pathogen. The interaction determines the severity of the infection. Therefore, successful cultivar development requires the ability to rapidly transfer genes or linkage blocks into desirable genetic backgrounds. Plant breeders must quickly introgress new resistance genes into the background of adapted cultivars.

This requirement for rapid advancement of generations during cultivar development is problematic when breeding winter wheat. Although winter wheat provides a desirable genetic background for breeding due to its ability to harden and withstand freezing temperatures, it can be difficult to manipulate during cultivar development because it requires vernalization (exposure to near freezing temperatures in the seedling stage) before flowering will occur.

Wheat breeders have accelerated the process of plant improvement by the use of off-season nurseries and/or greenhouses, thus allowing more generations to be grown per year. Three generations per year have been achieved in some spring wheat breeding programs for populations of restricked size grown in a greenhouse. However, most winter wheat breeders have been limited to one or two generations per year due to the vernalization requirement of winter wheat which may be as much as 65 days or longer depending upon the genotype.

Attempts have been made to shorten the generation time of wheat through acceleration of seed maturation, germination of immature seeds and green vernalization (Mukade, et al. (1973) 4*th Int. Wh. Genet. Symp.*:439). However, these procedures can be tedious in nature and require specific steps to be taken for each generation in an attempt to hasten generation advancement. Also, these procedures may not be effective with a broad spectrium of winter wheat genotypes.

Other attempts to achieve winter wheat objectives have involved DNA transformations. However, wheat transformation is currently difficult and relatively expensive (Vasil et al. (1992) *Bio/Technology* 10:667). Unpredicted deleterious somaclonal variation introduced to the recipient cultivar through the transformation process may prevent the direct use of transformed materials by farmers.

A need exists for methods providing rapid advancement of generations to facilitate cultivar development.

SUMMARY OF THE INVENTION

The present invention provides methods for rapidly advancing wheat generations towards a winter wheat objective which include crossing a winter wheat line with a donor line that has a dominant minimal vernalization gene to yield offspring that are heterozygous for the minimal vernalization gene and are capable of advancing three or more generations per year; breeding the heterozygous offspring; and selecting to recover wheat plants having the winter growth habit and/or winter hardiness. The offspring resulting from the breeding process may also be crossed with a winter wheat line before selection for winter hardiness or winter growth habit. The breeding step may include selecting for plants carrying the minimal vernalization gene. According to the present invention, the donor line may also have a gene or genes for desired traits.

It is an object of this invention to provide methods for rapidly advancing wheat generations.

It is another object of the present invention to provide convenient and efficient methods for achieving various breeding objectives which involve creating new, improved genotypes.

It is a further object of the present invention to provide cost-effective methods of obtaining improved wheat lines.

These and other objects, advantages and features are accomplished according to the compositions and methods of the following description of the preferred embodiment of the present invention.

DESCRIPTION OF THE PREFERRED EMBODIMENT

For the purposes of promoting an understanding of the principles of the invention, reference will now be made to the preferred embodiments thereof, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

As indicated above, the present invention provides methods for rapidly advancing wheat generations towards a winter wheat objective. The methods include crossing a winter wheat line with a donor line having a minimal vernalization gene, such as Vrn, breeding the offspring from that cross and either directly selecting winter growth habit plants, or crossing the offspring resulting from the cross with a winter wheat line to recover wheat plants having a winter growth habit.

According to the present invention, minimal vernalization genes may be used to achieve the advancement of three generations or more per year towards a winter wheat objective. The present invention capitalizes upon the dominance effects of the major genes conferring the spring growth habit (Morrison, (1960) Z. VererbLehre 91:141.). In spite of the substantial physiological differences between winter wheat and spring wheat, the genetic differences between them is relatively minor. The spring growth habit is thought to be controlled by no more than five genes, any one of which conferring the spring growth habit when a dominant allele is present.

Plant lines heterozygous for a major spring gene (such as Vrn) (Mcintosh and Cusick (1987) Wheat and Wheat Improvement:289.) may be grown to maturity with minimal vernalization. In this regard, vernalization refers to the artificial treatment of seeds before sowing or seedlings after germination to hasten flowering, and minimal vernalization is understood to mean a period of vernalization lasting no longer than about seven to ten days. Because the heterozygotes require only a minimal vernalization period, three generations or more per year may be achieved toward a winter wheat objective. Selection may be practiced during the breeding process for a Vrn gene and any desired gene(s) that are detectable under greenhouse conditions. After the final cross and identification of the gene(s) of interest, the selection can be reversed in relation to the dominant minimal vernalization gene so that the recessive gene types are favored and the winter growth habit is recovered. Resulting populations may then be directed to fall planted field nurseries for evaluation by standard field breeding methods.

Generally, the invention provides methods for new winter wheat cultivars which include crossing a winter wheat line having a winter growth habit with a donor line. It is understood that a "line" is a group of plants with characteristics that are distinct, uniform and stable. A line is preferably an inbred line which exhibits desirable characteristics such as yield, maturity, disease resistance and other agronomic or quality characteristics. Once a line is identified as being superior it may be named, increased, and made available commercially as a cultivated variety, or cultivar.

The winter wheat line may be any winter wheat, preferably an adapted, winter hardy wheat which provides a good genetic background. The donor line may be any wheat line having a dominant minimal vernalization gene. In one embodiment of the invention, the donor line may be obtained by crossing a wheat line having a desired trait with a spring wheat line requiring only minimal vernalization to yield the donor line.

In one embodiment of the invention, the donor line is a spring wheat line having a dominant Vrn gene. Offspring of crosses between donor and winter wheat parents are heterozygous, Vrn/vrn. Such heterozygotes have a spring growth habit and are capable of advancing three or more generations per year. According to the invention, a breeding process may be performed with the heterozygous offspring. The ability of the offspring to advance three or more generations per year due to the Vrn gene, is an improvement over the parent winter wheat line which is capable of only one or two generations per year due to the vernalization requirement.

The methods of the present invention may be used to rapidly advance inbreeding generations with or without selection. The breeding process may include selecting for plants carrying the minimal vernalization gene. It may also include selecting for and/or identifying plants which contain a desired trait or traits. After the final cross and identification of the desired genes, selection is reversed in relation to the minimal vernalization gene to favor the fully recessive types and recover the winter growth habit.

Preferably the desired trait is controlled by expression of a single dominant gene, but may be recessive or polygenic. The desired trait may relate to any one of several breeding objectives, including yield potential, yield stability, or grain quality. The desired trait may include resistance to disease, including wheat rush diseases, septoria tritici, septoria nodorum, powdery mildew, helminthosporium diseases, smuts and bunts, fusarium diseases, bacterial diseases, viral diseases, and others. The desired trait might provide improved yield, milling and baking ability, early maturity, or lodging resistance. The desired trait may be conferred by a dwarfing gene, including Rht. It may be grain color R (red wheat) or r (white wheat) glume color, hairiness, photoperiod response, homoeologous pairing, or male sterility M. The desired trait may included resistance to insect infestation, including Hessian fly, wheat stem soft fly, cereal leaf beetle, and green bug. Such traits are preferably conferred by a dominant gene such as the H21 gene for resistance to the Hessian fly [Mayetiola destructor, (Say)] but may be recessive or polygenic. Cytoplasmic traits such as male sterility (CMS) for hybrid wheat production may also be recombined with different nuclear genotypes. Fertility restorer for CMS Rf is also a trait of importance.

Where a particular Vrn gene and the gene of interest from a donor are discovered to be closely associated on the same chromosome, it will be preferable to use a different Vrn gene for the initial cross. In the case of close association of the genes, the difficulties related to repulsion phase linkage in the initial cross of a spring habit wheat by a donor or the coupling of the genes following cross over recombinations in later generations might significantly increase the effort required to utilize this method. However, these problems could be avoided by using a different Vrn gene. For example, if a gene for a trait such as Hessian fly resistance were located on the long arm of chromosome 5A near the Vrn1 locus, then a spring habit wheat line with a gene at the Vrn3 locus on the long arm of chromosome 5D or the Vrn5 on the short arm of chromosome 7B might be used instead to initiate the crossing program (Mcintosh and Cusick, 1987). This would not be possible in the case where the gene for introgression was already linked to a Vrn gene in a spring habit donor. In this case, crossover recombination would be the only way to effect the transfer into winker wheat.

Crosses made according to the methods of this invention may be accomplished by such conventional methods as are required to circumvent self-pollination. As is well known, the wheat flower is bi-sexual: wheat plants are practically always self-pollinated because the wheat anthers are located inside the florets and pollen is shed before flowers open. Generally, crosses can be accomplished as follows: Male anthers are removed from a plant to create a female plant. The head of the female plant is then covered to protect contamination. Pollen grain from anthers of the desired male plant are deposited on the stigmas of the female plant which remains covered to prevent contamination.

The techniques of the present invention may be used to facilitate various mating schemes including single, three way, four way, or more complex crosses. Numerous crossing and selection methodologies may be practiced including backcrossing, recurrent selection as well as other breeding schemes. It is understood that the term recurrent selection means a breeding system designed to increase the frequency of favorable genes of a quantitatively inherited characteristic by repeated cycles of selection. In backcross breeding schemes, a gene for a favorable trait may be added to an otherwise favorable cultivar. The most significant feature of the backcross is that it provides a means for changing an allele and a cultivar without otherwise affecting cultivar performance.

During the breeding process, selection may be made for the spring growth habit, i.e., minimal vernalization, by growing plants under a minimal vernalization regime. The minimal vernalization regime includes temperatures above 10° C., with temperatures not falling below 10° C. for more than about 7 to 10 days. Plants lacking a dominant vernalization gene will not flower under the minimal vernalization regime. At the same time, selection and/or screening for a desired trait may be carried out. For example, when the desired trait is insect resistance, plants may be exposed to the insect during the breeding process and seedlings may be screened for symptoms of infestation.

Various breeding methods may be utilized. For example, the heterozygous offspring may be back crossed with the recurrent parent having the winter growth habit. In a breeding scheme, a succession of backcrosses can be utilized to add a gene for a desirable character to an otherwise desirable parent, or the backcross may be made to concentrate genes for a quantitative character. The purpose of a backcross is to recover the genotype of the recurrent parent, except for the addition of a gene for the superior character. A recurrent parent is either an original parent or a genetic equivalent. The backcross is most useful if the character being added is simply inherited, dominant, and easily recognized in the hybrid plants. Backcrossing is a form of inbreeding, and the features of the recurrent parent are automatically recovered after successive backcrosses. The only selection practiced is for the one superior trait contributed by the recurrent parent. The plant selected from the final backcross progeny will be heterozygous for the desired trait.

According to the methods of the present invention, the back cross procedure may be repeated at least two more times, resulting in at least three generations in a twelve month period. Each time, a selection for progeny having a spring growth habit may be employed. It is understood that various breeding methods may be employed here. Thus, the offspring may be crossed with other various lines or with each other. Various wheat objectives may be screened for or selected.

After offspring have been obtained and the final selection for the trait of interest has occurred, the selection is then reversed so that recessive winter habit types are favored to recover the winter growth habit.

The offspring from the final back cross may then be evaluated by standard field breeding methods. Conventional methods may be used to establish a stable inbred line. For example, the seeds from a candidate plant may be planted in a head row (i.e., about 100 plants). The plants from the head row will be evaluated for the desired traits such as disease resistance or increased yield. The head row plants produce breeder seeds. The breeder seeds are planted and grown to make foundation seed. Where plants grown from the foundation seed have the desired characteristics, they will yield registered seed and, from these, certified seed.

A dynamic wheat germplasm "toolbox" consisting of a Vrn gene with genes of any number of various disease or insect resistance (or any other genes of importance) in the background of the best adapted elite winter germplasm available is contemplated. This "toolbox" may be accessed to "repair" new and promising elite materials that are deficient in one or more characters. Exceptional segregates with the character of interest and a Vrn allele may be used as an upgraded "tool" for the greenhouse germplasm "toolbox" to "repair" future elite lines.

In another embodiment, the methods of the present invention may also be used to rapidly introgress a recessive gene, but would require some additional effort since the trait of interest would not be phenotypically detectable in heterozygous individuals. The basic procedure would be essentially the same as for a dominant gene, but would require crossing with a number of random plants in each segregating generation. Self-pollinated seeds from these individual parent plants could then be grown concurrently with the backcross derived first filial generation (F1) plants. The second filial generation (F2) progeny plants could then be tested for the recessive trait. Families exhibiting the trait of interest would descend from heterozygous parent plants. Records of parent plants could then be referenced to determine which backcross families would be expected to be segregating for the gene to be transferred.

The segregating families would then be selected to repeat the process of crossing random individuals for the next generation and the non-segregating families would be discarded. In the case of the transfer of a single recessive gene, in each generation it would be necessary to cross with at least five random spring habit plants from segregating families in order to be confident (P<0.05) of at least one plant being heterozygous for the gene of interest. Sixteen or more plants from a segregating family would be necessary to begin each backcrossing cycle so that one could be confident (P<0.05) of recovering at least five spring habit plants for crossing. In practice, twenty five plants or more are recommended to start each cycle, when working with a recessive gene. An increased number of plants helps protect against the effects of poor germination or other growing problems and enhances the probability of recovering the desired genotypes.

Rapid generation advance via Vrn genes according to the present invention, provides an efficient means to manipulate genes introduced to wheat via DNA transformation technologies. Transfer of genes to adapted types according to this invention is easier and less expensive than repeated attempts at transfers in each new wheat background.

The methods of this invention may also be used to facilitate a recurrent selection program for improved yield by modifying the technique proposed by Frey et al. ((1988) *Crop Sci.* 28:855.) to account for unvernalized winter habit segregates by measuring yield on the basis of individual plant yield per se. Precise determination of quantitatively inherited traits, such as yield, may not be possible with small populations in greenhouse or hill plot experiments. However, breakthroughs in wheat yield improvement have historically resulted from certain specific crosses that have demonstrated a high frequency of very exceptional segregates. Crosses of this nature may represent the favorable recombination of relatively large and positive linkage blocks from the parents. The methods of the present invention may be used to effectively screen large numbers of crosses in early generation greenhouse and hill plot experiments to quickly identify these very outstanding crosses and recycle selections into the recurrent selection program. Tillering potential may be a major influence on per se yield in a 10 cm pot or a space planted field transplant, and that high tillering types may prove to be more tolerant to Hessian fly infestation, as well as a number of other production hazards. Tillering may also be a major component of yield stability in the 18 cm. rows which are commonly used by soft red winter wheat producers.

In the following example, an apparent single gene from the FL85238-G28-G4 parent was used to effect the minimal vernalization requirement. If more than one Vrn gene were utilized in the initial cross, a lower minimum number of heterozygous plants would be necessary in each generation since spring habit segregates would be much more frequent. However, winter habit segregates would be less frequent in later generations. It is therefore preferred to use a single Vrn gene to initiate the crossing and to follow throughout the breeding generations.

The skilled artisan will be able to ascertain, with a minimum amount of experimentation, the various desired genetic backgrounds and genes for the various traits that may be incorporated into those backgrounds in accordance with the methods of the present invention.

The following specific example is provided for purposes of illustrating the invention, and no limitations on the invention are intended thereby.

EXAMPLE

Materials and Methods

IN8138I1-16-5-50 is a Purdue University soft red winter wheat experimental line that possesses superior winter hardiness but is susceptible to Hessian fly biotype "L". This line was chosen as the recurrent parent in a backcrossing program to transfer H21, a dominant Hessian fly resistance gene carried on the chromosome arm 2RL of 'Chaupon' rye (*Secale cereal* L.) (Friebe et al., 1990). KS86HF012-23-6, a hard red winter wheat germplasm line developed at Kansas State University which carries the translocation 2BS/2RL, was used as the donor of H21. FL85238-G28-G4 is a University of Florida experimental soft red winter wheat line that can be grown with minimal vernalization (less than seven days) and probably possesses one of the major Vrn genes or an allele. It is unknown whether FL85238-G28-G4 possesses a named Vrn gene or a gene as yet undescribed. However, it is not essential to know which minimal vernalization gene is present in order to utilize the gene to effect the desired rapid generation advancement. FL85238-G28-G4 was chosen as the source for the minimal vernalization gene because of its good soft wheat quality and the package of assembled disease resistance genes that allow it to perform well in the warm and humid conditions of southeastern USA.

Hessian fly Biotype L was used to screen segregating families because it has the greatest number of genes for virulence of Hessian fly biotypes identified to date (Sofa, 1981). Biotype L can infest wheats with genes H3 to H8 and H11. Wheat seedlings were grown in greenhouse flats 54×36×8 cm. and tested for Hessian fly resistance as described previously (Maas et al., (1989) *Crop. Sci.* 29:23.)

Germinating seeds were placed in a controlled chamber maintained at 4° C. to 5° C. after planting to break dormancy and enhance the uniformity of germination, thus reducing the probability of late germinating plants that may escape Hessian fly infestation. Presumably, this period could provide some minimal vernalizing effect for certain Vrn alleles and may be responsible for causing an earlier heading date in the greenhouse than otherwise would have been observed. No other cold chamber treatment was used for plants carrying the Vrn gene during the generations of backcrossing. Several plants of the IN8138I1-16-5-50 recurrent parent were vernalized using standard vernalization techniques, 4° C. to 5° C. for 60 days or longer. Transplants were moved to the greenhouse at weekly intervals so that synchronous flowering would be assured for each crossing generation.

Seedlings without obvious symptoms of infestation (stunting, dark green color) were removed from the flat and examined for the presence of dead first instar larvae behind the lead sheath to avoid advancing non-infested susceptible escapes. Resistant plants were transplanted into 10 cm plastic pots containing greenhouse soil. The unvernalized resistant transplants and vernalized plants of the recurrent parent were grown to maturity under a 24 hr. photoperiod. For the first six weeks in the greenhouse, night temperatures were held near 10° C., when possible, while an attempt was made to keep day time temperatures below 25° C.

Subsequently, night temperatures were increased to 20° C. until harvest. After pollination, day temperatures were allowed to vary between 25° C. and 35° C. All-purpose fertilizer was applied regularly as a liquid solution three or four times per growing cycle.

Ten F1 plants of the cross: KS86HF012-23-6/FL85238-G28-G4 were grown in the greenhouse between July and November. These F1's were transplanted at intervals in order to synchronize flowering with fully vernalized IN813811-16-5-50 plants. The three way cross: IN8138I1-16-5-50//KS86HF012-23-6/FL85238-G28-G4 was made. The three way F1's generated from this cross were screened for resistance to Hessian fly biotype L. IN8138I1-16-5-50 was used as the seed parent in this cross and in subsequent generations of backcrossing, so that both the H21 gene and the Vrn gene would be genetic markers to insure that no self-pollinated plants were advanced. Plants lacking the H21 gene would not survive the Hessian fly infestation, and plants lacking the Vrn gene would not flower under the minimal vernalization regime. The resistant three way F1 seedlings were grown in the greenhouse from November 1991 to March 1992 and backcrossed to the IN8138I1-16-5-50 recurrent parent. The BC1 plants were screened to Hessian fly and transplanted to the field in April 1992, and BC2 crosses were made in June using vernalized IN8138I1-16-5-50 plants that had been transplanted to the field. The BC2 F1 plants were selected for Hessian fly resistance and grown to produce BC2 F2 seed. The BC2 F2 families were tested to verify that the Hessian fly resistance was present.

Results and Discussion

In a backcrossing program, progeny of heterozygous dominant individuals backcrossed to the recessive recurrent parent are expected to segregate in a ratio of 1:1. This was observed for both the H21 gene and the Vrn gene (data for the Vrn gene not presented). At least one plant in each generation was found to be both resistant to Hessian fly and also capable of flowering without vernalization (Table 1).

TABLE 1

Reaction of progeny to Hessian fly biotype L during successive generations of a backcrossing program to introduce the H21 gene into the background of IN8138I1-16-5-50 by using a Vrn gene to avoid lengthy vernalization periods each generation.

| Cross | Parentage | No. of Seeds | Number of plants Resistant | Susceptible |
|---|---|---|---|---|
| | BC0 generation - November to March | | | |
| 92898A | IN8138I1-16-5-50//<br>KS86HF012-23-6/<br>FL85238-G28-G4 | 6 | 2 | 4 |
| | BC1 generation - March to July | | | |
| 922642A | IN8138I1-16-5-50*2//<br>KS86HF012-23-6/<br>FL85238-G28-G4 | 16 | 10 | 6 |
| | BC2 generation - July to November | | | |
| 922816A | IN8138I1-16-5-50 *3//<br>KS86HF012-23-6/<br>FL85238-G28-G4 | 5 | 2 | 3 |
| | BC2 F2 progeny test - November | | | |
| 922816A1 | IN8138I1-16-5-50 *3//<br>KS86HF012-23-6/<br>FL85238-G28-G4 | 35 | 31 | 4 |

The use of procedures according to this invention are illustrated in the Example by a backcrossing program, employing a Vrn gene for the transfer of the dominant H21 gene for resistance to Hessian fly [*Mayetiola destructor*, (Say)] biotype "L" into the background of IN8138I1-16-5-50, a winter hardy, experimental soft red winter wheat line susceptible to biotype L. BC2 F1 individuals heterozygous for both the H21 gene and a Vrn gene were developed within twelve months.

This Example provides merely one illustration of one embodiment of the invention. The methods of this invention may be used to create a dynamic germplasm "toolbox" consisting of any of a number of genes for various resistances or other traits in association with a Vrn gene in the background of adapted elite winter wheats. These methods may also be used to facilitate other crossing schemes or recurrent selection.

While the invention has been described in detail in the foregoing description, the same is to be considered as illustrative and not restrictive in character, it being understood that only the preferred embodiments have been shown and described, and that all changes and modifications that come within the spirit of the invention are desired to be protected.

All publications cited herein are hereby incorporated by reference in their entirely as if each had been individually incorporated by reference and fully set forth.

What is claimed is:

1. A method for rapidly advancing wheat generations to develop a winter wheat plant, comprising:
   (a) crossing a winter wheat line having a winter growth habit with a donor line having a dominant minimal vernalization gene; harvesting first seed from said crossing step; and planting the first seed to yield first offspring that are heterozygous for the minimal vernalization gene, and have a spring growth habit and are capable of advancing three or more generations per year;
   (b) conducting a breeding program which includes advancing three generations of progeny of the first offspring within a one-year period, said advancing three generations of progeny including harvesting seed resulting from the breeding of progeny of an immediately prior generation, planting the seed, and breeding plants produced from the seed, said breeding including selecting for plants carrying the minimal vernalization gene;
   (c) after conducting said breeding program, selecting to recover wheat plants having winter growth habit; and
   (d) harvesting and planting the seed of the wheat plants selected in step (c) to produce winter wheat plants with winter growth habit.

2. The method of claim 1 further comprising crossing offspring resulting from said breeding with a wheat line having a winter growth habit before selecting to recover wheat plants having winter growth habit.

3. The method of claim 1 wherein the minimal vernalization gene is a dominant Vrn gene.

4. The method of claim 1 wherein the step of selecting in step (c) includes a backcross with the winter wheat line.

5. The method of claim 1 further comprising crossing a first wheat line having a desired trait with a second wheat line requiring no more than minimal vernalization; harvesting seed resulting from said crossing: and planting the seed to produce the donor line.

6. The method of claim 5 wherein the second line contains at least one copy of a Vrn gene.

7. The method of claim 5 wherein the desired trait is a controlled by the expression of a dominant gene.

8. The method of claim 5 wherein the desired trait includes resistance to a disease.

9. The method of claim 5 wherein the desired trait provides improved yield.

10. The method of claim 9 wherein the desired trait is conferred by a dwarfing gene.

11. The method of claim 10 wherein the dwarfing gene is selected from the group consisting of $Rht_1$, $Rht_2$, and $Rht_3$.

12. The method of claim 5 wherein the desired trait includes resistance to insect infection.

13. The method of claim 12 wherein the insect is selected from the group consisting of Hessian fly, wheat stem sawfly, cereal leaf beetle, and green bug.

14. The method of claim 13 wherein the desired trait is conferred by the H21 gene.

15. The method of claim 5 wherein the desired trait includes early maturity.

16. The method of claim 5 wherein the desired trait includes lodging resistance.

17. The method of claim 5 wherein the desired trait is resistance to rust disease.

18. The method of claim 1 wherein the breeding program includes recurrent selection.

19. The method of claim 1 wherein the breeding program includes backcrossing to the winter wheat line as the recurrent parent.

20. A breeding method for producing a winter wheat carrying a gene of interest, comprising:

(a) crossing a first winter wheat line having the vernalization genotype vrn/vrn with a spring wheat line having the vernalization genotype Vrn/Vrn; harvesting first seed from said crossing step; and planting the first seed to produce a heterozygous wheat having the vernalization genotype Vrn/vrn;

(b) introducing the gene of interest into said heterozygous wheat, said introducing resulting from the spring wheat line in step (a) carrying the gene of interest or from crossing the heterozygous wheat with one or more additional wheat lines carrying the gene of interest, harvesting seed from said crossing, and planting the harvested seed; and (c) breeding the heterozygous wheat, said breeding including advancing three generations of progeny of the heterozygous wheat per year by harvesting seed resulting from the breeding of progeny of an immediately prior generation, planting the seed, and breeding plants produced from the seed; and (d) crossing plants from said breeding step (c) with a wheat plant having a vrn gene, harvesting seed from said crossing, and planting the seed to produce a second winter wheat line having the vernalization genotype vrn/vrn and carrying the gene of interest.

21. The method of claim 20 wherein said breeding step includes backcrossing the heterozygous wheat line with the first winter wheat line.

22. The method of claim 21 wherein said breeding step includes backcrossing and selecting a plant resulting from the backcross and inbreeding the plant.

23. The method of claim 20 wherein the introducing step results from a three or more way cross.

24. The method of claim 20 wherein gene of interest is selected from the group consisting of insect resistance, disease resistance and semi-dwarfism.

* * * * *

UNITED STATES PATENT AND TRADEMARK OFFICE
CERTIFICATE OF CORRECTION

PATENT NO. : 5,682,708
DATED : November 4, 1997
INVENTOR(S) : Frederick B. Maas, III It is certified that error appears in the above-indentified patent and that said Letters Patent is hereby corrected as shown below:

In col. 2, line 14, please delete "Hatcherr" and insert in lieu thereof --Hatchett--.

In col. 5, line 35, please delete "winker" and insert in lieu thereof --winter--.

In col. 9, line 10, please delete "IN813811" and insert in lieu thereof --IN8138I1--.

In col. 10, line 62, please delete ":" and insert in lieu thereof --;--.

Signed and Sealed this

Seventeenth Day of February, 1998

*Attest:*

BRUCE LEHMAN

*Attesting Officer*     Commissioner of Patents and Trademarks